US00PP14476P29

(12) United States Plant Patent
Lamb

(10) Patent No.: US PP14,476 P2
(45) Date of Patent: Jan. 20, 2004

(54) ANTHURIUM PLANT NAMED 'MISTY ROSE'

(50) Latin Name: *Anthurium hybrid*
Varietal Denomination: Misty Rose

(75) Inventor: Ann Elizabeth Lamb, Sebring, FL (US)

(73) Assignee: Twyford International, Inc., Santa Paula, CA (US)

( * ) Notice: Subject to any disclaimer, the term of this patent is extended or adjusted under 35 U.S.C. 154(b) by 0 days.

(21) Appl. No.: 10/313,119

(22) Filed: Dec. 6, 2002

(51) Int. Cl.[7] ..... A01H 5/00
(52) U.S. Cl. ..... Plt./365
(58) Field of Search ..... Plt./365

*Primary Examiner*—Kent L. Bell
(74) *Attorney, Agent, or Firm*—C. A. Whealy

(57) ABSTRACT

A distinct cultivar of Anthurium plant named 'Misty Rose', characterized by its upright and outwardly spreading plant habit; glossy dark green-colored leaves; flat, cordate and pink-colored spathes; inflorescences that are positioned among and above the foliage on strong and erect scapes; and excellent inflorescence longevity with spathes maintaining pink coloration for at least eight weeks.

1 Drawing Sheet

Botanical classification/cultivar designation: Anthurium hybrid cultivar Misty Rose.

BACKGROUND OF THE INVENTION

The present invention relates to a new and distinct cultivar of Anthurium plant, botanically known as Anthurium hybrid, and hereinafter referred to by the cultivar name 'Misty Rose'.

The new Anthurium is a product of a planned breeding program conducted by the Inventor in Apopka, Fla. The objective of the breeding program is to create new Anthurium cultivars with a rapid growth rate, dark green-colored foliage and uniform flowering habit.

The new Anthurium originated from a cross-pollination made by the Inventor in Apopka, Fla. on Apr. 23, 1997, of the Anthurium hybrid cultivar Pura Vida Red, disclosed in U.S. Plant Pat. No. 9,080, as the female, or seed, parent with the Anthurium hybrid cultivar Cotton Candy, disclosed in U.S. Plant Pat. No. 8,819, as the male, or pollen, parent. The cultivar Misty Rose was discovered and selected by the Inventor as a flowering plant within the progeny of the stated cross-pollination in a controlled environment in Apopka, Fla., on May 11, 2000.

Asexual propagation of the new cultivar by meristem culture in a controlled environment in Sebring, Fla., since July, 1997, has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature, daylength and light intensity, without, however, any variance in genotype.

The following traits have been repeatedly observed and are determined to be the unique characteristics of the cultivar Misty Rose. These characteristics in combination distinguish 'Misty Rose' as a new and distinct cultivar of Anthurium:

1. Upright and outwardly spreading plant habit; relatively intermediate in size.
2. Glossy dark green-colored leaves.
3. Flat, cordate and pink-colored spathes.
4. Inflorescences that are positioned among and above the foliage on strong and erect scapes.
5. Excellent inflorescence longevity with spathes maintaining pink coloration for at least eight weeks.

Plants of the new Anthurium are most similar to plants of the male parent, the cultivar Cotton Candy. In side-by-side comparisons conducted in Homestead, Fla., plants of the new Anthurium differed from plants of the cultivar Cotton Candy in the following characteristics:

1. Plants of the new Anthurium were taller and more upright than plants of the cultivar Cotton Candy.
2. Leaves of plants of the new Anthurium were larger than leaves of plants of the cultivar Cotton Candy.
3. Leaf petioles and scapes of plants of the new Anthurium were flushed with bronze whereas leaf petioles and scapes of plants of the cultivar Cotton Candy were green in color.
4. Spathes of plants of the new Anthurium were larger and darker pink in color than spathes of plants of the cultivar Cotton Candy.

Plants of the new Anthurium can also be compared to plant of the female parent, the cultivar Pura Vida Red. In side-by-side comparisons conducted in Homestead, Fla., plants of the new Anthurium differed from plants of the cultivar Pura Vida Red in the following characteristics:

1. Plants of the new Anthurium were more durable and better suited to commercial production than plants of the cultivar Pura Vida Red.
2. Spathes of plants of the new Anthurium were pink in color whereas spathes of plants of the cultivar Pura Vida Red were dark red in color.

BRIEF DESCRIPTION OF THE PHOTOGRAPH

The accompanying colored photograph illustrates the overall appearance of the new Anthurium, showing the colors as true as it is reasonably possible to obtain in colored reproductions of this type. Colors in the photographs may differ slightly from the color values cited in the detailed botanical description which accurately describe the colors of the new Anthurium. The photograph comprises a side perspective view of a typical 14 month old flowering plant of the cultivar Misty Rose grown in a 20-cm container.

DETAILED BOTANICAL DESCRIPTION

The following observations and measurements describe 14-month old plants grown in 20-cm containers in Homestead, Fla., in a polypropylene-covered shadehouse with day temperatures of 21 to 32° C., night temperatures of 18 to 24° C., and light levels about 1,500 foot-candles.

In the following description, color references are made to The Royal Horticultural Society Colour Chart, 1995 Edition, except where general terms of ordinary dictionary significance are used.

Botanical classification: Anthurium hybrid cultivar Misty Rose.

Parentage:

*Female, or seed, parent.*—Anthurium hybrid Pura Vida Red, disclosed in U.S. Plant Pat. No. 9,080.

*Male, or pollen, parent.*—Anthurium hybrid Cotton Candy, disclosed in U.S. Plant Pat. No. 8,819.

Propagation:

*Type.*—Asexual; by meristem culture.

*Time to initiate roots on a meristem*-cultured plant.—About 10 to 12 days at day temperatures of 21 to 32° C. and night temperatures of 18 to 24° C.

*Time to develop roots on a meristem-cultured plant.*—About 147 days at day temperatures of 21 to 32° C. and night temperatures of 18 to 24° C.

*Root description.*—White-colored thick fleshy roots with fine lateral roots; root tip, 183C in color.

Plant description:

*Plant shape.*—Upright and outwardly spreading plant habit, inverted triangle, symmetrical; relatively intermediate in size.

*Growth habit.*—Freely clumping, bushy and dense growth habit.

*Plant height, soil level to top of leaf canopy.*—About 46 to 53 cm.

*Plant diameter or spread.*—About 55 to 65 cm.

*Foliage description.*—Length: About 17 to 21 cm. Width: About 12 to 17.5 cm. Shape: Deltoid to somewhat cordate. Apex: Acuminate. Base: Truncate to somewhat cordate. Margin: Entire; somewhat undulate. Texture, upper and lower surfaces: Leathery; glabrous. Luster, upper and lower surfaces: Glossy. Aspect: Flat or slightly convex between the veins on the upper surface. Venation: Midvein with well-defined primary veins radiating out from the petiole junction. Midvein protrudes from the upper surface for about 75% of the leaf length. Primary veins protrude on the lower surface. There are about four to six primary veins per leaf. Petiole: Length: About 24 to 31 cm. Diameter, just below the geniculum: About 5 mm. Geniculum: Length: About 2.9 cm. Diameter: About 5.5 mm. Orientation: Typically curved. Petiole sheath: Length: About 3 cm. Width, at midpoint: About 5 mm. Apex: Rounded. Cataphyll: New leaves emerge from a cataphyll which turns brown with subsequent development and eventually abscises. Length: 10 to 14 cm. Width, at base: About 2.5 cm. Shape: Triangular. Apex: Acute, apiculate. Margin: Entire. Texture, upper and lower surfaces: Smooth. Color: Developing leaves, upper surface: 147A, flushed with 166A. Developing leaves, lower surface: 147B to 147C, flushed with 166A. Fully expanded leaves, upper surface: Closest to, but greener than 139A. Lower leaf surface: 146B. Midrib, developing leaves, upper and lower surfaces: 146C. Midrib, fully expanded leaves, upper surface: 146B. Midrib, fully expanded leaves, lower surface: 145A. Petiole: 146B, flushed with 183B. Geniculum: 146B, flushed with 183B. Petiole sheath: 145A, flushed with 182A. Cataphyll, upper surface: 182C. Cataphyll, lower surface: 178C.

Inflorescence description:

*Inflorescence arrangement.*—When developing, the spathe is tightly rolled around the spadix and emerges from the petiole sheath. The spathe is fully opened approximately when the peduncle is fully elongated. Spathes with spadices held among and above the foliage on straight wiry peduncles and open vertically. Inflorescences are typically grouped in the center of the plant. Freely and continuous flowering year-round; about nine open inflorescences and about four flower buds per plant at one time.

*Inflorescence longevity.*—Inflorescences maintain good color and substance on the plant for at least eight weeks. As cut flowers, inflorescences maintain good color and substance for about two to three weeks. Inflorescences persistent.

*Time to flower.*—First flowers develop about seven months after planting 20-week old rooted plants.

*Spathe.*—Length: About 7.5 to 8.8 cm. Width: About 5.6 to 6.6 cm. Shape: Ovate. Apex: Cuspidate, terminated by a long curved apicula. Base: Cordate. Margin: Entire. Texture, upper and lower surfaces: Leathery; glabrous. Aspect: Initially cupped, flattening with development. Color: Fully opened, front surface: Closest to, but more pink than 47A. Fully opened, back surface: 5IA to 51B. Faded, front and back surfaces: 48B to 48C, streaked with 147A; apicula, 145A.

*Spadix.*—Length: About 4.6 to 5.9 cm. Diameter: About 7.5 mm. Shape: Columnar. Cross section: Rounded. Longitudinal axis: Erect. Color: When the spathe unrolls, the spadix is closest to, but lighter than 158B, becoming 150D at the apex. When the spathe is fully open, the spadix changes color to 69B, becoming closest to, but lighter than 180D at the apex. When the spathe has faded, spadix becomes 147C, tinged wth 173C.

*Reproductive organs.*—Androecium: Anthers and filaments are minute and not clearly visible. Pollen, white in color, close to 155D. Gynoecium: Pistils are translucent white and protrude between the staminate flowers and extend about 0.5 mm beyond the stamens.

*Scape.*—Length: About 50 to 59 cm. Aspect: Strong and erect, wiry. Color: 147B, flushed with 183B.

*Fruit.*—Shape: Oblong to elliptic. Length: About 5 mm. Diameter: About 3 mm. Color: 144A, tinged with 20D when ripe; flesh, translucent yellow/orange, 22D.

*Seed.*—Quantity per fruit: One or two. Quantity per inflorescence: About 150. Shape: Elliptic, often somewhat flattened. Length: About 3 mm. Diameter: About 2 mm. Color: 145B.

Disease/pest resistance: Under commercial conditions, plants of the new Anthurium have not been observed to be resistant to pathogens or pests common to Anthurium.

Temperature tolerance: Plants of the new Anthurium have been observed to be tolerant to temperatures ranging from 7 to 40° C.

It is claimed:

1. A new and distinct cultivar of Anthurium plant named 'Misty Rose', as illustrated and described.

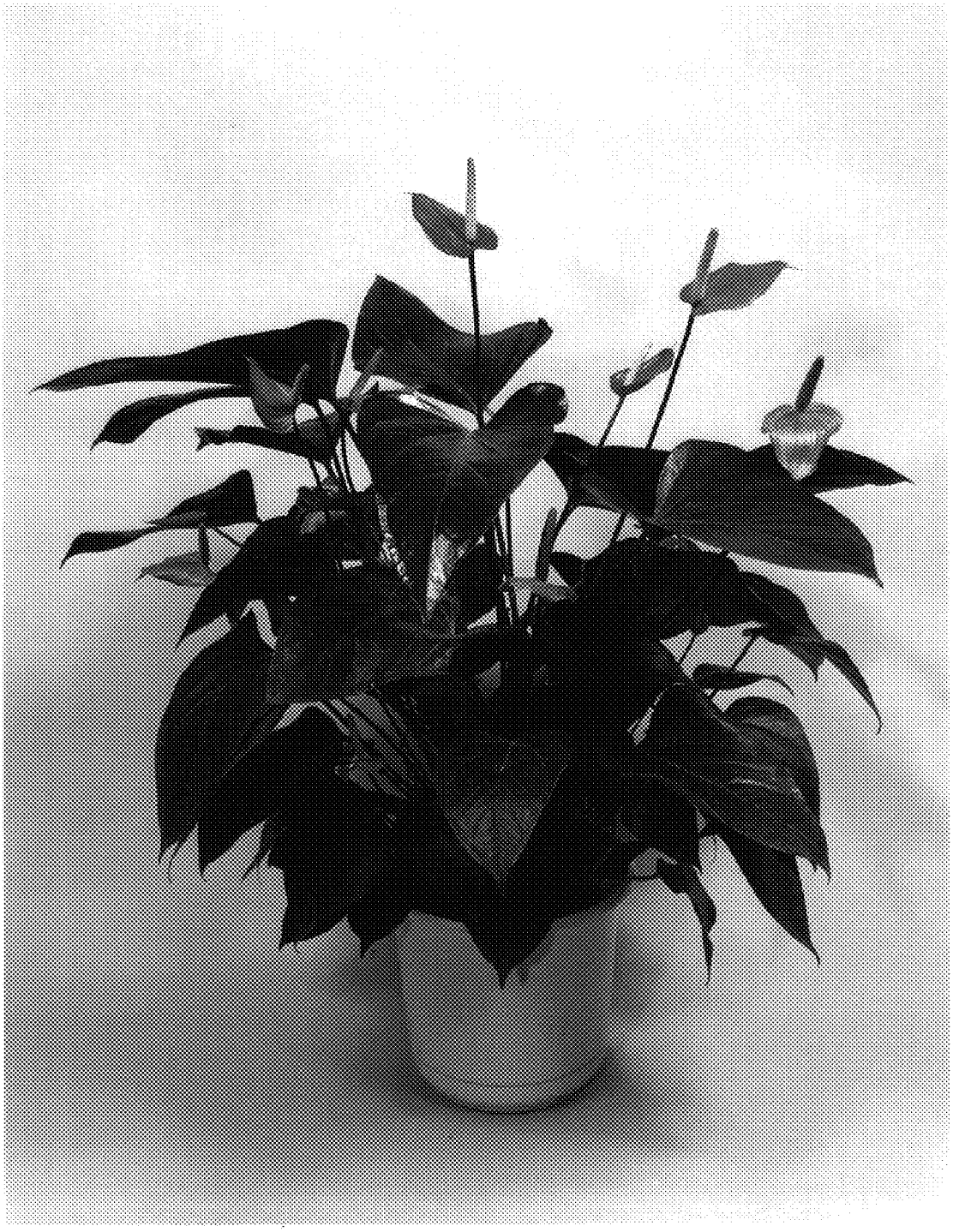

* * * * *